United States Patent [19]

DeBoer et al.

[11] Patent Number: 5,279,999

[45] Date of Patent: Jan. 18, 1994

[54] CATALYST COMPOSITION

[75] Inventors: Eric J. M. DeBoer; Koen Steernberg, both of Amsterdam, Netherlands

[73] Assignee: Shell Oil Company, Houston, Tex.

[21] Appl. No.: 967,902

[22] Filed: Oct. 27, 1992

[30] Foreign Application Priority Data

Oct. 28, 1991 [EP] European Pat. Off. ......... 91202784.4

[51] Int. Cl.$^5$ .............................................. C08F 4/64
[52] U.S. Cl. ...................................... 502/117; 502/103; 526/160; 526/348; 556/53
[58] Field of Search ................................. 502/103, 117

[56] References Cited

U.S. PATENT DOCUMENTS

| | | | |
|---|---|---|---|
| 4,530,914 | 7/1985 | Ewen et al. | 502/103 X |
| 4,937,299 | 6/1990 | Ewen et al. | 502/117 X |
| 5,077,255 | 12/1991 | Welborn | 502/117 X |
| 5,086,025 | 2/1992 | Chang | 502/117 |
| 5,104,956 | 4/1992 | Waymouth | 502/117 X |
| 5,126,301 | 6/1992 | Tsutsui et al. | 502/103 X |
| 5,126,303 | 6/1992 | Resconi et al. | 502/117 |

FOREIGN PATENT DOCUMENTS

| | | |
|---|---|---|
| 283739A2 | 9/1988 | European Pat. Off. |
| 316155A2 | 5/1989 | European Pat. Off. |

OTHER PUBLICATIONS

J. of Organometallic Chem., vol. 417, No. 1-2, Jan. 10, 1991, Lausanne, CH, pp. 9–27, P. Burger, "Ansa-Metallocene Derivatives".
Search report dated Dec. 28, 1992.

*Primary Examiner*—Patrick P. Garvin
*Attorney, Agent, or Firm*—Otto O. Meyers, III

[57] ABSTRACT

A catalyst composition obtained by contacting (a) a Group IVA metal compound of the general formula

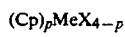

$$(Cp)_p MeX_{4-p}$$

wherein Cp is, independently, cyclopentadienyl groups substituted with one or more hydrocarbyl groups, and at least one cyclopentadienyl group is substituted with a single, optionally substituted, aryl group, Me is a Group IVA metal, X is one or more non-cyclopentadienyl substituents attached to the Group IVA metal, wherein the substituents are hydrocarbyl groups, hydrocarboxy groups, hydrocarbamide groups, hydrogen or halogen, and p is an integer of from 1 to 4; and (b) an aluminoxane. Further, a process for polymerizing one or more alpha-olefins by contacting the one or more alpha-olefins with the catalyst composition of the invention to produce polymers.

13 Claims, No Drawings

CATALYST COMPOSITION

FIELD OF THE INVENTION

This invention relates to a catalyst composition and a process for the polymerization of one or more alpha-olefins comprising contacting the alpha-olefin(s) with the catalyst composition.

BACKGROUND OF THE INVENTION

Catalyst compositions based upon a Group IVA metal compound of the general formula $(Cp)_2MeX_2$ wherein Cp represents identical or different cyclopentadienyl groups which may be substituted with one or more alkyl groups, Me represents a Group IVA metal and X represents halogen substituents attached to the Group IVA metal, and an aluminoxane are known. Further, the use of such catalyst compositions in the polymerization of one or more alpha-olefins is known from EP-A-283739.

In order to be effective in the polymerization, the known catalyst compositions contain a relatively large amount of the aluminoxane component. Such polymers typically contain a high amount of residual catalyst and further, the polymerization process is not cost effective.

The polymerization of alpha-olefins having at least three carbon atoms with a catalyst composition having cyclopentadienyl groups which are mono-, di-, tri- or tetraalkyl substituted, producing polyolefin polymers having a vinylidene end group are known. When propylene or butene-1 are polymerized, the polymer end group is of the formula $-C(CH_3)=CH_2$ or $-C(C_2H_5)=CH_2$, respectively. The application of polymers having a vinylidene end group, as an intermediate in the preparation of additives for lubricating oil compositions is the subject of the European patent application 0490454.

Various documents, such as EP-A-129368, EP-A-226463, EP-A-128046 and EP-A-260999, disclose polymerization catalyst compositions containing cyclopentadienyl Group IVA metal compounds and an aluminoxane. These documents teach that the cyclopentadienyl groups can be unsubstituted or substituted with a wide variety of hydrocarbyl groups, such as alkyl, arylalkyl, alkenyl, aryl and alkylaryl, but they do not indicate a preference for aryl or alkylaryl groups. For example, they do not contain any example of compounds with an aryl or alkylaryl substituted cyclopenta-dienyl group. The documents further teach that any number of alkyl groups can be present on the cyclopentadienyl group. For example, bis(cyclopentadienyl)zirconium compounds can have alkyl, dialkyl, trialkyl, tetraalkyl or pentaalkyl substituted cyclopentadienyl groups.

Although there are many well known high activity catalysts, it is still desired to improve the activity of the catalyst and produce polymers having a vinylidene substituent.

SUMMARY OF THE INVENTION

The present invention provides catalyst compositions which have a high activity in the polymerization of alphaolefins. More particularly, the present invention relates to catalyst compositions comprising (a) a Group IVA metal compound of the general formula

wherein Cp is, independently, cyclopentadienyl groups which are substituted with one or more hydrocarbyl groups and at least one cyclopentadienyl group is substituted with a single, optionally substituted, aryl group, Me is a Group IVA metal, X is one or more non-cyclopentadienyl substituent attached to the Group IVA metal and p is an integer from 1 to 4; and (b) an aluminoxane.

Further, the invention relates to a process for the polymerization of one or more alpha-olefins comprising contacting the alpha-olefins with the catalyst composition of the present invention.

BRIEF DESCRIPTION OF THE INVENTION

The catalyst compositions of the invention are based on Group IVA metal compounds of the general formula $(Cp)_pMeX_{4-p}$ wherein Cp is, independently, cyclopentadienyl groups, which are substituted with one or more hydrocarbyl groups and at least one of the cyclopentadienyl groups is substituted with only one optionally substituted aryl group. According to the formula, p is an integer of 1 to 4. It is preferred that p equals 2. Me is a Group IVA metal. Metals of Group IVA are those metals of Group IV as defined in the Periodic Table of the Elements, IUPAC, published in Kirk-Othmer, Encyclopedia of Chemical Technology, 2nd edition, Vol. 8, p. 94. Suitable Group IVA metals include zirconium and hafnium. The preferred Group IVA metal is zirconium. X is one or more substituents on the Group IVA metal substituents.

It is preferred that each cyclopentadienyl group is substituted with one aryl group. The aryl groups attached to the cyclopentadienyl groups may be identical or different. Examples of suitable aryl groups are naphthyl groups, phenyl and biphenyl groups. The preferred aryl groups are phenyl groups.

Optionally, the aryl groups are substituted. If the aryl group is substituted, it is substituted with one or more hydrocarbyl groups, such as alkyl, or aryl groups, alkyloxy groups and dialkylamino groups, halogenated hydrocarbyls, hydrocarbyl groups containing heteroatoms or halides. The alkyloxy and dialkylamino groups, when present, are preferably shielded, for example by a neighboring substituent, hereinafter identified as a "shielding group." When the aryl group is substituted with alkyloxy groups, it is preferred that the alkyloxy group have up to 10 carbon atoms, such as methoxy, ethoxy, isopropoxy, t-butoxy, hexyloxy and 2-decyloxy groups. Suitable shielding groups are bulky alkyl groups, such as cycloalkyl and t-alkyl groups having up to 10 carbon atoms, e.g. t-butyl groups or t-amyl groups, and aryl groups having up to 10 carbon atoms. The preferred shielding groups are t-alkyl groups such as t-butyl and t-amyl groups.

The position of the optional substituents at the aryl group, relative to the cyclopentadienyl group to which the aryl group is attached, is not critical. When the aryl group is a phenyl group, the substituents on the phenyl group are positioned at the para and/or meta positions.

Attached to the Group IVA metal are one or more non-cyclopentadienyl substituents, as represented by X in the general formula. X substituents, independently, are hydrocarbyl groups, hydrocarboxy groups, hydrocarbamide groups, hydrogen and halogen. The term hydrocarboxy includes alkyloxy and aryloxy groups and the term hydrocarbamide includes alkylamide and arylamide groups. It is preferred that X is hydrocarbyl group and/or halogen. It is further preferred that X is one or more hydrocarbyl groups of up to 20 carbon atoms, with hydrocarbyl groups of up to 10 carbon atoms being more preferred. The preferred hydrocarbyl groups are phenyl groups and alkyl groups of up to 6 carbon atoms. The preferred alkyl group is a methyl group. Where X is a halogen, it is preferred that the halogen is chlorine.

Suitable (Cp) components include phenylcyclopentadienyl, (4-t-butylphenyl)cyclopentadienyl, (2-methylphenyl)cyclopentadienyl, (2-ethylphenyl)cyclopentadienyl, (2-i-propylphenyl)cyclopentadienyl, (4-chlorophenyl)cyclopentadienyl, (3,5-di-t-butylphenyl)cyclopentadienyl, (3,5-di-t-butyl-2-4-methyloxyphenyl)cyclopentadienyl, (3,5-di-t-butyl-2-methyloxyphenyl)cyclopentadienyl, (3,5-di-t-butyl-2-methyloxyphenyl)cyclopentadienyl, and mixtures thereof.

As it is preferred that Me is zirconium and X is chlorine, zirconium dichloride based Group IVA metal components are particularly preferred.

The Group IVA metal compounds of the present catalyst compositions are novel compounds. Accordingly, the present invention also relates to Group IVA metal compounds of the general formula wherein $(Cp)_p MeX_{4-p}$ wherein Cp, Me, X and p have the previously stated meanings.

The novel Group IVA metal compounds can be prepared by methods which are known per se. For example, bis(arylcyclopentadienyl)zirconium dichlorides are prepared by reacting arylcyclopentadienyllithium with zirconium tetrachloride. The preparation of arylcyclopentadienyllithium compounds is accomplished by reacting a corresponding arylcyclopentadiene with n-butyllithium.

Arylcyclopentadienes are prepared by methods known per se. For example, arylcyclopentadienes are prepared by reacting an aryl bromide with n-butyllithium and reacting the obtained aryllithium with a cyclopentenone. The adduct of the aryllithium and the cyclopentenone, thus obtained, is subsequently treated with an acid to obtain the arylcyclopentadiene.

Exemplary of suitable Group IVA metal compounds, according to the invention, include bis(phenylcyclopentadienyl)zirconium dichloride, bis[(4-t-butylphenyl)cyclopentadienyl]zirconium dichloride, bis[(2-methylphenyl)cyclopentadienyl]zirconium dichloride, bis[(2-ethylphenyl)cyclopentadienyl]zirconium dichloride, bis[(2-i-propylphenyl)cyclopentadienyl]zirconium dichloride, bis[(4-chlorophenyl)cyclopentadienyl]zirconium dichloride, bis[(3,5-di-t-butylphenyl)cyclopentadienyl]zirconium dichloride, bis[(3,5-di-t-butyl-4-methyloxyphenyl)cyclopentadienyl]zirconium dichloride, (cyclopentadienyl)(3,5-di-t-butyl-4-methoxyphenylcyclopentadienyl)zirconium dichloride, bis(3,5-di-t-butyl-2-methoxyphenylcyclopentadienyl)zirconiumdichloride, (cyclopentadienyl)(3,5-di-t-butyl-2-methoxyphenylcyclopentadienyl)zirconium dichloride, bis[(4-t-butylphenyl)cyclopentadienyl]hafnium dichloride, bis(3-methoxyphenylcyclopentadienyl)hafnium dichloride, bis(3-methoxyphenylcyclopentadienyl)zirconium dichloride and mixtures thereof.

The catalyst compositions of the invention further comprise an aluminoxane. Aluminoxane are compounds represented by the general formulae $(R-Al\leq O)_q$, which represents a cyclic compound, and $R(RAl-O)_q-AlR_2$, which represents a linear compound. In these general formulae, R is an alkyl group of 1 to 5 carbon atoms, such as methyl, ethyl, isobutyl or isopropyl and q is an integer of from 1 to 100. It is preferred that q is an integer in the range from 5 to 20. Further, it is more preferred that R is a methyl group. The preferred aluminoxanes are methylaluminoxane, isobutylaluminoxane, isopropylaluminoxane, ethylaluminoxane and mixtures thereof, with methylaluminoxane being more preferred. The aluminoxanes are suitably prepared by reacting water with trialkylaluminium compounds by methods known in the art. A mixture of linear and cyclic compounds is usually obtained.

The molar ratio of aluminoxane to Group IVA metal compound (calculated as gram atom of aluminum per gram atom of Group IVA metal) may vary. Preferably the molar ratio of aluminoxane to the Group IVA is from about 2 to about 10000, with molar ratio from about 50 to about 2000 being more preferred.

The catalyst composition of the present invention is prepared from the Group IVA metal compound and the aluminoxane prior to the contacting with the alpha-olefin to be polymerized. In an alternative embodiment, the catalyst composition is prepared in situ, i.e. in the presence of alpha-olefin. It is preferred to prepare the catalyst composition by mixing together the two components in a solvent such as toluene or chlorobenzene to form a liquid catalyst system.

In the present polymerization process one or more olefins are contacted with the catalyst composition of this invention. Suitable α-olefins are ethylene, propylene, hexene, styrene. The preferred olefins are aliphatic α-olefins of up to 10 carbon atoms, inclusive. Preferably the catalyst composition is used to polymerize propylene.

The polymerization process is preferably carried out at a temperature of from about −60° to about 200° C., with a temperature range from about 0° to about 100° C. being more preferred. Pressures from about 0.1 to about 500 bar. It is preferred that the pressure is from about 1 bar to about 100 bar. The optimum conditions of temperature and pressure used for a particular catalyst composition to maximize the yield of the desired polymer having the desired molecular weight can readily be established by those skilled in the art.

The present polymerization process is generally carried out in an inert liquid solvent such as toluene, chlorobenzene or chlorotoluene. Selection of such inert liquid solvent is broadly within the skill of the art. Polymerization is carried out in batch or continuous operation. The polymerization is suitably carried out in the absence of air or moisture. Reaction times of from 5 minutes to 72 hours have been found to be suitable, depending on the activity of the catalyst. If desired, a conventional catalyst deactivating agent such as a proton donor may be added to the reaction mixture to terminate the polymerization, after a suitable reaction time.

Sufficient quantity of the catalyst system is employed in the reaction mixture such that the mixture contains from about $10^{-2}$ to about $10^{-7}$ gram atom of Group IVA metal per liter volume of reaction mixture. It is preferred that quantity of catalyst system contain from about $10^{-3}$ gram atom to about $10^{-6}$ gram atom of the Group IVA metal per liter volume of the reaction mixture.

According to one embodiment of the invention, polymerization of α-olefins using the catalyst composition produces polymers having a number average molecular weight amount from about 200 to about 50,000. In a preferred embodiment of the invention, the number average molecular weight is from about 300 to about 10,000. A more preferred embodiment has a number average molecular weight from about 700 to about 5,000 being more preferred. In these preferred embodiments, the molecular weight distribution is such that the ratio of weight-average molecular weight to the number-average molecular weight amounts is from about 1.1 to about 5.0. The more preferred embodiments have a ratio of weight-average molecular weight to number-average molecular weight amounts of from about 1.6 to about 2.4.

As stated hereinbefore, the molecular weight of the resulting polymer is controlled by a selection of the temperature and the pressure of the polymerization reaction mixture for a given combination of a catalyst composition and one or more alpha-olefins. It is known in the art that, in addition, the molecular weight of the polymer is controlled by polymerizing in the presence of hydrogen.

The polymers prepared in the present process are recovered by conventional techniques, such as removing the solvent and/or the unreacted olefin by evaporation. Further, catalyst remnants are removed from the polymer by conventional means such as, washing or extracting the polymer with a suitable liquid.

Polymers prepared according to the present process are converted to succinimide derivatives by reaction with maleic anhydride and subsequently with an amine. It is preferred that the amine has 1 to 50 carbon atoms. It is further preferred that the amine is of the general formula H—(NH—(CH$_2$)$_m$)$_n$—NH$_2$ wherein m is an integer of from 2 to 4 and n is an integer of from 1 to 9. Succinimide derivatives prepared as described above, in particular those which are based on an atactic polypropylene having a number-average molecular weight from 700 to 5000 and substantially having vinylidene end groups, are useful as dispersant additives in lubricating oil compositions.

The invention described herein is illustrated, but not limited by the following examples. The experimental procedures were carried out with rigorous exclusion of oxygen and water, unless water was involved as one of the reactants, or unless indicated otherwise.

EXAMPLE 1

Preparation of bis[(4-t-butylphenyl)cyclopentadienyl]zirconium dichloride.

A solution of 34 g of 4-t-butylphenylbromide (0.16 mole) in 50 ml diethyl ether was slowly added to a stirred mixture of 100 ml of a solution of n-butyllithium in hexane (1.6 mole/l) and 50 ml diethyl ether, while the temperature of the mixture was kept at $-25\,°$ C. After completion of the addition, the temperature of the resultant mixture was allowed to rise slowly to about room temperature. Subsequently the temperature was decreased to $-25°$ C. and 13.2 g of 2-cyclopentene-1-one (0.16 mole) dissolved in a small volume of diethyl ether was slowly added. The suspension thus obtained, was allowed to reach room temperature and then stirred for one hour. An excess amount of water was added to the suspension to result in 1-(4-t-butylphenyl)cyclopentanol. The 1-(4-t-butylphenyl)cyclopent-2-en-1-ol product was isolated from the reaction mixture by extraction with diethyl ether and subsequently purified by chromatography over silica, using dichloromethane as the elution solvent.

A solution of 7 g of 1-(4-t-butylphenyl)cyclopent-2-en-1-ol (0.032 mole) and 0.1 g of p-toluenesulphonic acid (0.00058 mole) in 70 ml toluene was gently heated to 40° C. for 5 minutes. The mixture was washed with aqueous sodium hydroxide and subsequently with water. After drying the organic phase over magnesium sulphate for 2 hours, 20.3 ml of a solution of n-butyllithium in hexane (1.6 mole/liter, 0.032 mole n-butyllithium) was added. A precipitate was formed and the precipitate was washed three times with hexane to obtain 4-t-butylphenylcyclopentadienyllithium as an off-white solid material.

A solution of 1.2 g of 4-t-butylphenylcyclopentadienyllithium (0.0059 mole) in 20 ml tetrahydrofuran was slowly added at room temperature to a solution of 0.685 g of zirconium tetrachloride (0.0029 mole) in 50 ml tetrahydrofuran. After stirring the solution for 2 hours, the tetrahydrofuran was removed by evaporation leaving a residue. The resulting residue was taken up in hot toluene. Any undissolved material was removed by filtration and a resultant clear solution was evaporated to dryness. The solid residue obtained from the evaporation to dryness was taken up in dichloromethane. Undissolved, off-white solids were removed by centrifugation and decantation. The clear solution was once again evaporated to dryness yielding bis[(4-t-butylphenyl)cyclopentadienyl]zirconium dichloride as a yellow solid material. Spectral data from a proton-NMR is consistent with the product obtained.

EXAMPLES 2-8

Preparation of various bis(arylcyclopentadienyl)zirconium dichlorides

The method outlined in Example 1 was essentially repeated, except that 4-t-butylphenylbromide, 1-(4-t-butylphenyl)cyclopent-2-en-1-ol and 4-t-butylphenylcyclopentadienyllithium were replaced by equimolar quantities of various arylbromides and the corresponding 1-arylcyclopent-2-en-1-ols and arylcyclopentadienyllithiums, respectively. The intermediate products obtained were 1-arylcyclopent-2-en-1-ols and arylcyclopentadienyllithiums.

The spectral data, as measured by proton-NMR spectroscopy, of bis(4-t-butylphenylcyclopentadienyl)zirconium dichloride, bis(phenylcyclopentadienyl)zirconium dichloride, bis(2-methylphenylcyclopentadienyl)zirconium dichloride, bis(2-ethylphenylcyclopentadienyl)zirconium dichloride, bis(2-i-propylphenylcyclopentadienyl)zirconium dichloride, bis(3,5-di-t-butylphenylcyclopentadienyl)zirconium dichloride, bis(3,5-di-t-butyl-4-methloxyphenyl)cyclopentadienyl)zirconium dichloride and bis(4-chlorophenyl)cyclopentadienyl)zirconium dichloride are consistent with the structure of these compounds.

EXAMPLE 9 (For Comparison)

Preparation of bis(1,2-diphenylcyclopentadienyl)zirconium dichloride

Glutaryl chloride (28.2 g; 0.167 mole) was slowly added to a mixture of anhydrous aluminum trichloride (50 g; 0.375 mole) and 250 ml benzene. The mixture was stirred vigorously in an ice/water bath. After completion of the addition, the ice/water bath was removed and stirring was continued for two hours. The solution obtained was slowly poured into a mixture of 200 g crushed ice and 40 ml concentrated aqueous hydrochloric acid. The resulting product was recovered by extraction and crystallization to produce 1,5-diphenyl-1,5-pentanedione.

A suspension of zinc powder (7.8 g; 0.12 mol) in 20 ml tetrahydrofuran was added slowly to a mixture of 1,5-diphenyl-1,5-pentanedione (5.0 g; 0.02 mol) and titanium tetrachloride (11.4 g; 0.06 mol) in 500 ml tetrahydrofuran. The mixture was kept at −10° C. After additional stirring at 0° C. for 5 hours, the mixture obtained was made basic by the addition of a 10% aqueous solution of potassium carbonate. The resulting 1,2-diphenyl-1,2-cyclopentanediol product was recovered by extraction.

A mixture of 1,2-diphenyl-1,2-cyclopentanediol (1.2 g; 0.0048 mole), activated 4A molecular sieves and a small amount of p-toluenesulphonic acid in 40 ml benzene was heated at 70° C. for 30 minutes. The mixture was filtered at room temperature. A solution (3.0 ml) of n-butyllithium in hexane (1.6 mole/liter, 0.0048 mole n-butyllithium) was added to the filtrate. After 45 minutes of stirring, a solution of zirconium tetrachloride (0.56 g; 0.0024 mole) in tetrahydrofuran was slowly added. After stirring the mixture at 65° C. for three hours, the solvents were evaporated. The solid material obtained was taken up in dichloromethane and centrifuged. The supernatant liquid was decanted and evaporated to dryness. The residue was washed with hexane and crystallized from toluene.

EXAMPLE 10 (For Comparison)

Preparation of bis(1,2,4-triphenylcyclopentadienyl)zirconium dichloride

The methods outlined in comparative Example 9 were essentially repeated except that glutaryl chloride, 1,5-diphenyl-1,5-pentanedione and 1,2-diphenyl-1,2-cyclopentanediol were replaced by equimolar quantities of 3-phenylglutaryl chloride, 1,3,5-triphenyl-1,5-pentanedione and 1,2,4-triphenyl-1,2-cyclopentanediol, respectively. The intermediate products obtained were 1,3,5-triphenyl-1,5-pentanedione and 1,2,4-triphenyl-1,2-cyclopentanediol, respectively.

EXAMPLE 11 (For Comparison)

Preparation of bis(1,2,3-triphenylcyclopentadienyl)zirconium dichloride

The methods outlined in comparative Example 9 were essentially repeated except that glutaryl chloride, 1,5-diphenyl-1,5-pentanedione and 1,2-diphenyl-1,2-cyclopentanediol were replaced by equimolar quantities of 2-phenylglutaryl chloride, 1,2,5-triphenyl-1,5-pentanedione and 1,2,3-triphenyl-1,2-cyclopentanediol, respectively. The intermediate products obtained were 1,3,5-triphenyl-1,5-pentanedione and 1,2,4-triphenyl-1,2-cyclopentanediol, respectively.

EXAMPLE 12 (For Comparison)

Preparation of bis(1,3-diphenylcyclopentadienyl)zirconium dichloride

A mixture of 8.1 g (0.03 mol) 3-benzyl-5-(2-hydroxyethyl)-4-methyl-1,3-thiazolium chloride, 180 ml triethylamine, 150 ml ethanol, 21 g of 1-butene-3-one (0.3 mol) and 30.7 g of benzaldehyde (0.29 mol) was gently stirred at 80° C. for 16 hours. Volatile components were removed by evaporation. The 1-phenyl-1,4-pentanedione thus formed was recovered by extraction and subsequent vacuum distillation.

A mixture of 9.7 g of 1-phenyl-1,4-pentanedione (0.055 mole), 500 ml of water, 15 g of sodium hydroxide and 1000 ml of ethanol was heated under reflux for 4 hours. The mixture was allowed to cool to room temperature and was then neutralized with acid. Ethanol was evaporated. The 3-phenylcyclopent-2-en-1-one formed was recovered by extraction and crystallization.

A mixture of 7.9 g (0.050 mole) of bromobenzene in 15 ml tetrahydrofuran was slowly added to a mixture of 34 ml of a solution of n-butyllithium in hexane (1.6 mole/liter, 0.055 mole n-butyllithium) and 40 ml of tetrahydrofuran at −80° C. At −40° C., 4.7 g (0.030 mole) of 3-phenylcyclopent-2-en-1-one in a small amount of tetrahydrofuran, was slowly added to the mixture. The resultant mixture was allowed to reach room temperature. Methanol and water were added. The 1,3-diphenylcyclopentadiene formed was recovered by extraction and crystallization.

A solution (1.4 ml) of n-butyllithium in hexane (1.6 mole/liter, 0.0023 mole n-butyllithium) at 80° C. was added slowly to 0.50 g (0.0023 mole) of 1,3-diphenylcyclopentadiene dissolved in 20 ml tetrahydrofuran. The mixture thus obtained was allowed to reach room temperature. A mixture of 0.268 g (0.00115 mole) of zirconium tetrachloride in 10 ml tetrahydrofuran was slowly added. After stirring the mixture for two hours, the solvents were evaporated. The solid material obtained was taken up in toluene and centrifuged. The supernatant was decanted and cooled to −20° C. The crystallized product was recovered by filtration.

EXAMPLES 13–23

Polymerization of propylene

A solution of 0.30 g of a purchased sample of methylaluminoxane, dissolved in toluene, was siphoned into an evacuated, mechanically stirred autoclave which was kept at 20° C., and subsequently propylene was introduced to obtain and maintain a pressure of 6.0 bar. In Examples 13–19 the temperature was maintained at 20° C. and in Examples 20–23 the temperature was increased to 30° C. A sample of a zirconium compound (0.00001 mole) dissolved in toluene was injected into the autoclave by means of an injection device. The injection device was immediately rinsed with toluene which was added to the contents of the autoclave thus bringing the total volume of n toluene to about 250 ml. The reaction times applied in the various Examples were in the range of from 15 minutes (for a reaction with a relatively high reaction rate) to 2.5 hours (for a reaction with a relatively low reaction rate). The reaction was terminated by releasing the pressure in the autoclave and subsequently removing the remaining volatile materials under reduced pressure at a temperature of up to 80° C. The polymer obtained was weighed and analyzed by $^1$H-NMR and $^{13}$C-NMR for determination of the number-average molecular weight.

This procedure was carried out using, as the zirconium compound, bis(cyclopentadienyl)zirconium dichloride and bis(mono-, di- and triarylcyclopentadienyl)zirconium dichlorides as specified in Table 1. The bis(mono-, di- and triarylcyclopentadienyl)zirconium dichlorides were prepared as indicated in Examples 1–5 and 8–12, respectively.

The average rates of polymerization and the number-average molecular weights of the polymer products are given in Table 2. The NMR-spectra revealed that the polymers were atactic polypropylenes and that the end groups present was vinylidene end groups, i.e., groups of the formula —C(CH$_3$)=CH$_2$, and n-propyl groups. The vinylidene and n-propyl groups were present at about a 1:1 molar ratio.

TABLE 1

| Example | Substituent(s) at cyclopentadienyl (Cp)$_2$ group | Polymerization rate$^a$ | Molecular weight$^b$ |
|---|---|---|---|
| a. Unsubstituted bis-cyclopentadienyl | | | |
| 13$^c$ | — | 15 | 650 |
| b. Bis-monoarylcyclopentadienyl | | | |
| 14 | 4-t-butylphenyl | 53 | 5500 |
| 15 | phenyl | 53 | 3900 |
| 16 | 2-methylphenyl | 51 | 4300 |
| 17 | 2-ethylphenyl | 76 | 2200 |
| 18 | 2-i-propylphenyl | 45 | 4400 |
| 19 | 4-chlorophenyl | 28 | 3300 |
| c. Bis-diarylcyclopentadienyl | | | |
| 20$^c$ | phenyl (1,2-substitution on CP ring) | 13 | ≧20000 |
| 21$^c$ | phenyl (1,3-substitution on Cp ring) | 28 | ≧20000 |
| d. Bis-triarylcyclopentadienyl | | | |
| 22$^c$ | phenyl (1,2,3-substitution on Cp ring) | 13 | 1150 |
| 23$^c$ | phenyl (1,2,4-substitution on Cp ring) | 10 | 2650 |

$^a$10$^3$ mole propene/(mole Zirconium/hour), reaction temperature 20° C., unless indicated otherwise
$^b$number-average molecular weight
$^c$for comparison, not according to invention

EXAMPLES 24–28

Polymerization of propylene

The methods outlined in comparative Example 13 were essentially repeated except that the reaction temperature was 45° C. instead of 20° C. and that a different methyaluminoxane was used.

The procedure was carried out using bis(cyclopentadienyl)zirconium dichloride, bis(monoarylcyclopentadienyl)zirconium dichlorides and bis(monomethylcyclopentadienyl)zirconium dichloride as specified in Table 2. The bis(monoarylcyclopentadienyl)zirconium dichlorides were prepared as indicated in Examples 1, 6 and 7.

The average rates of polymerization and the number-average molecular weights of the polymer products are given in Table 3.

The NMR-spectra revealed that the polymers were atactic polypropylenes and that vinylidene end groups, i.e. groups of the formula —C(CH$_3$)=CH$_2$, and n-propyl groups, were present. The vinylidene and n-propyl groups were present at about a 1:1 molar ratio.

TABLE 2

| Example | Substituent at cyclopentadienyl (Cp)$_2$ group | Polymerization rate$^a$ | Molecular weight$^b$ |
|---|---|---|---|
| a. Unsubstituted bis-cyclopentadienyl | | | |
| 24$^c$ | — | 150 | 600 |
| b. Bis-monoarylcyclopentadienyl | | | |
| 25 | 4-t-butylphenyl | 300 | 5400 |
| 26 | 3,5-di-t-butylphenyl | 450 | 8500 |
| 27 | 3,5-di-t-butyl-4-methyloxyphenyl | 280 | 3800 |
| c. Bis-monoalkylcyclopentadienyl | | | |
| 28$^c$ | methyl | 85 | 1200 |

$^a$10$^3$ mole propene/(mole Zirconium/hour), reaction temperature 45° C.
$^b$number-average molecular weight
$^c$for comparison, not according to invention

EXAMPLES 29–33

Polymerization of propylene

The methods outlined in comparative Examples 24–28 were essentially repeated except that a different methylaluminoxane was used.

The procedure was carried out using two bis(monoarylcyclopentadienyl)zirconium dichlorides and two (cyclopentadienyl)(arylcyclopentadienyl)zirconium dichlorides as specified in Table 3. They were prepared as indicated in Example 1, except that 4-methoxy-3,5-di-t-butylphenylbromide, 2-methoxy-3,5-di-t-butylphenylbromide and 3-methoxy-phenyl bromide were used instead of 4-t-butylphenylbromide in examples 29, 30, and 33, respectively, and cyclopentadienyl zirconium trichloride was used instead of zirconium tetrachloride in examples 31 and 32.

The average rates of polymerization and the number-average molecular weights of the polymer products are given in Table 4. The NMR-spectra revealed that the polymers were atactic polypropylenes and that vinylidene groups, i.e. groups of the formula —C(CH$_3$)=CH$_2$, and n-propyl groups were present. The vinylidene and n-propyl groups were present at about a 1:1 molar ratio.

TABLE 3

| Example | Cyclopentadienyl (Cp)$_2$ group | Polymerization rate$^a$ | Molecular weight$^b$ |
|---|---|---|---|
| 29 | Bis(3,5-di-t-butyl-4-methyloxy-phenylcyclopentadienyl | 200 | 3200 |
| 30 | (Cyclopentadienyl)(3,5-di-t-butyl-2-methyloxyphenylcyclopentadienyl | 100 | 590 |
| 31 | Bis(3,5-t-butyl-2-methyloxy-phenylcyclopentadienyl) | 1.2 | 1200 |
| 32 | (Cyclopentadienyl)(3,5-di-t-butyl-2-methyloxyphenyl-cyclopentadienyl) | 50 | 400 |
| 33 | Bis(3-methyloxyphenylcyclopentadienyl) | 0.5 | 1100 |

$^a$10$^3$ mole propene/(mole Zirconium/hour), reaction temperature 45° C.
$^b$number-average molecular weight

EXAMPLES 34–37 (For Comparison)

Polymerization of propylene

The methods outlined in comparative Example 13 were essentially repeated using 1,2-ethylene-bis(indenyl)zirconium dichloride, 1,2-ethylene-bis(3-phenylindenyl)zirconium dichloride, 1,2-ethylene-bis[3-(4-methylphenyl)indenyl]zirconium dichloride or 1,2-ethylene-bis[3-(3,5-dimethyl-4-methyloxyphenyl)indenyl]zirconium dichloride as the zirconium compound.

The average rates of polymerization and the number-average molecular weights of the polymer products are given in Table 4.

TABLE 4

| Example | Aryl | Polymerization rate$^a$ | Molecular weight$^b$ |
|---|---|---|---|
| a. Unsubstituted 1,2-ethylene-bisindenyl | | | |
| 34$^c$ | — | 25 | 15000 |
| b. 1,2-ethylene-bis(3-arylindenyl) | | | |
| 35$^c$ | phenyl | 30 | 31000 |
| 36$^c$ | 4-methylphenyl | 25 | 28000 |
| 37$^c$ | 3,5-dimethyl-4-methyloxyphenyl | $^d$ | $^d$ |

$^a$10$^3$ mole propene/(mole Zirconium/hour)
$^b$number-average molecular weight
$^c$for comparison, not according to invention
$^d$polymerization rate was very low, no measurement

What is claimed is:

1. A catalyst composition comprising:

(a) a Group IVA metal compound of the general formula $$(Cp)_p MeX_{4-p}$$

wherein Cp is, independently, cyclopentadienyl groups substituted with one or more hydrocarbyl groups and at least one cyclopentadienyl group is substituted with a single, substituted or unsubstituted aryl group, Me is a Group IVA metal, X is one or more non-cyclopentadienyl Group IVA metal substituents selected from the group consisting of hydrocarbyl groups, hydrocarboxy groups, hydrocarbamide groups, hydrogen, halogen, and mixtures thereof, and p is an integer of from 1 to 4; and (b) an aluminoxane.

2. The catalyst composition of claim 1 wherein the aryl group is substituted with one or more groups.

3. The catalyst composition according to claim 2, wherein the aryl group is a phenyl group.

4. The catalyst composition according to claim 3, wherein the phenyl group is substituted with one or more groups selected from the group consisting of cycloalkyl groups, aryl groups, alkyloxy groups, dialkylamino groups, halogenated hydrocarbyls and halides.

5. The catalyst composition according to claim 4 wherein the group is a dialkylamino or alkyloxy groups.

6. The catalyst composition according to claim 5 wherein group is substituted with one or more shielding groups selected from the group consisting of alkyl groups and cycloalkyl groups.

7. The catalyst composition according to claim 6, wherein the shielding group is a t-alkyl group having up to 10 carbon atoms.

8. The catalyst composition according claim 7, wherein the Group IVA metal is zirconium or hafnium.

9. The catalyst composition according to claim 8 wherein the Group IVA metal is zirconium.

10. The catalyst composition according to claim 9, wherein X is chlorine.

11. The catalyst composition according to claim 10, wherein the molar ratio of aluminoxane to the Group IVA metal compound is within the range of from 2 to 10000, calculated as gram atom aluminoxane per gram atom Group IVA metal.

12. The catalyst composition according to claim 11, wherein the Group IVA metal compound is bis(phenylcyclopentadienyl)zirconium dichloride, bis[(4-t-butylphenyl)cyclopentadienyl]zirconium dichloride, bis[(2-methylphenyl)cyclopentadienyl]zirconium dichloride, bis[(2-ethylphenyl)cyclopentadienyl]zirconium dichloride, bis[(2-i-propylphenyl)cyclopentadienyl]zirconium dichloride, bis[(4-chlorophenyl)cyclopentadienyl]zirconium dichloride, bis[(3,5-di-t-butylphenyl)cyclopentadienyl]zirconium dichloride, bis[(3,5-di-t-butyl-4-methyloxyphenyl)cyclopentadienyl]zirconium dichloride, (cyclopentadienyl)(3,5-di-t-butyl-4-methoxyphenylcyclopentadienyl)zirconium dichloride, bis(3,5-di-t-butyl-2-methoxyphenylcyclopentadienyl)zirconium dichloride, (cyclopentadienyl)-(3,5-di-t-butyl-2-methoxyphenylcyclopentadienyl)zirconium dichloride or bis(3-methoxyphenylcyclopentadienyl)zirconium dichloride.

13. The catalyst composition according to claim 12, wherein the aluminoxane is methylaluminoxane, ethylaluminoxane, isopropylaluminoxane, isobutylaluminoxane or mixtures thereof.

* * * * *